United States Patent
Yotsutsuji

(10) Patent No.: US 10,456,527 B2
(45) Date of Patent: Oct. 29, 2019

(54) GASKET USING MEDICAL SILICONE RUBBER HAVING SLIDABILITY, AND SYRINGE USING SAID GASKET

(71) Applicant: Coki Engineering Inc., Osaka-shi, Osaka (JP)

(72) Inventor: Akira Yotsutsuji, Osaka (JP)

(73) Assignee: COKI ENGINEERING INC., Osaka (JP)

( * ) Notice: Subject to any disclaimer, the term of this patent is extended or adjusted under 35 U.S.C. 154(b) by 165 days.

(21) Appl. No.: 15/501,377

(22) PCT Filed: Apr. 24, 2015

(86) PCT No.: PCT/JP2015/002245
§ 371 (c)(1),
(2) Date: Feb. 2, 2017

(87) PCT Pub. No.: WO2016/056149
PCT Pub. Date: Apr. 14, 2016

(65) Prior Publication Data
US 2017/0232202 A1    Aug. 17, 2017

(30) Foreign Application Priority Data
Oct. 7, 2014    (WO) .................. PCT/JP2014/005104

(51) Int. Cl.
*A61M 5/315* (2006.01)
*A61M 5/28* (2006.01)
(Continued)

(52) U.S. Cl.
CPC ....... *A61M 5/31513* (2013.01); *A61L 31/028* (2013.01); *A61L 31/041* (2013.01);
(Continued)

(58) Field of Classification Search
CPC .... A61M 5/31513; A61M 5/28; A61M 5/315; A61L 31/048; C08L 23/06; C08L 2207/068
See application file for complete search history.

(56) References Cited

U.S. PATENT DOCUMENTS

2006/0233991 A1\* 10/2006 Humphrey ................ A61F 2/07
428/36.91
2010/0204658 A1\* 8/2010 Imai .................. A61M 5/31513
604/222
(Continued)

FOREIGN PATENT DOCUMENTS

CN    1802417 A    7/2006
CN    1863837 A    11/2006
(Continued)

OTHER PUBLICATIONS

Machine translation of JP 2007 054621, performed Oct. 11, 2018.\*
(Continued)

*Primary Examiner* — Bradley J Osinski
(74) *Attorney, Agent, or Firm* — Lucas & Mercanti, LLP

(57) ABSTRACT

A syringe is to be obtained by using PTFE for a gasket main body that makes a direct contact with an injection solution and using a slidable silicone rubber at a portion that does not make contact with the injection solution.
A syringe A includes a syringe barrel 1, a gasket 10 press-fitted within the syringe barrel 1, and a plunger rod 5 mounted in the gasket 10. In the gasket 10, a concaved groove 18 is formed over the whole circumference of a slide-contact surface 11 of a main body portion 26 that is formed of a rigid plastic having a drug solution-resistant property against a drug solution 30 to be loaded in the syringe barrel 1 and that is configured to slidingly contact an inner circumferential surface 2 of the syringe barrel 1. In a slide-contact ring 19 that is to be fitted in the concaved
(Continued)

groove 18 and that is configured to slidingly contact the syringe barrel inner circumference surface 2, a silicone oil and a spherical ultrahigh molecular weight fine powder are added to a silicone rubber base material 19*c*.

10 Claims, 6 Drawing Sheets

(51) Int. Cl.
*C08L 23/06* (2006.01)
*C08L 83/04* (2006.01)
*A61L 31/02* (2006.01)
*A61L 31/04* (2006.01)
*A61L 31/14* (2006.01)

(52) U.S. Cl.
CPC .............. *A61L 31/048* (2013.01); *A61L 31/14* (2013.01); *A61M 5/28* (2013.01); *A61M 5/315* (2013.01); *C08L 23/06* (2013.01); *C08L 83/04* (2013.01); *A61M 2205/025* (2013.01); *A61M 2205/0222* (2013.01); *A61M 2205/0238* (2013.01); *C08L 2203/02* (2013.01); *C08L 2205/14* (2013.01); *C08L 2207/068* (2013.01)

(56) References Cited

U.S. PATENT DOCUMENTS

2013/0102994 A1* 4/2013 Gibler ................. A61M 5/1452
604/506
2013/0338606 A1* 12/2013 Conzone ........... A61M 5/31513
604/230

FOREIGN PATENT DOCUMENTS

| JP | H05131029 A | 5/1993 |
|----|----|----|
| JP | 2006159819 A | 6/2006 |
| JP | 2007054621 A | 3/2007 |
| JP | 2009505794 A | 2/2009 |
| JP | 5406416 B1 | 2/2014 |
| WO | 2009001600 A1 | 12/2008 |
| WO | 2011122574 A1 | 10/2011 |

OTHER PUBLICATIONS

Machine translation of JPH05131029, performed Oct. 11, 2018.*
Office Action of Japanese Patent Application No. 2015-551913 corresponding to the PCT International Application No. PCT/JP2015/002245 issued by JPO dated Mar. 8, 2016.
International Search Report dated Aug. 11, 2015 for Application No. PCT/JP2015/002245 and English translation.
Office Action dated Jan. 2, 2019 from the corresponding Chinese Patent Application No. 201580028017.0.

* cited by examiner

SLIDING RESISTANCE MEASUREMENT RESULTS

SYRINGE BARREL INTERNAL DIAMETER: Φ 6.20
SEAL WIDTH S: 0.1, 0.6, 2 mm
TEST SPEED: 100 mm/min SYRINGE BARREL INTERNAL DIAMETER: Φ 6.20
SEAL WIDTH S: 0.1 mm
TEST SPEED: 100 mm/min

SLIDING RESISTANCE MEASUREMENT RESULTS OF COMPOSIT GASKET

GASKET USING MEDICAL SILICONE RUBBER HAVING SLIDABILITY, AND SYRINGE USING SAID GASKET

CROSS REFERENCE TO RELATED APPLICATION

This Application is a 371 of PCT/JP2015/002245 filed on Apr. 24, 2015 which, in turn, claimed the priority of Japanese International Patent Application No. PCT/JP2014/005104 filed on Oct. 7, 2014, both applications are incorporated herein by reference.

TECHNICAL FIELD

The present invention relates to a gasket having a new structure that enables elimination of a silicone grease from gaskets for injection syringes including those that are disposable and particularly from gaskets for pre-filled syringes, in which application of the silicone grease to the inner surface of a syringe barrel (cylindrical tube) has been conventionally regarded as essential. In further detail, the present invention relates to a gasket having a new structure using a rigid plastic such as PTFE (polytetrafluoroethylene) for a gasket main body that makes a direct contact with the injection solution and using, in order to ensure sealability and slidability of the gasket, a medical silicone rubber having slidability at a portion that does not make contact with an injection solution. Furthermore, the present invention relates to a syringe using the new gasket.

BACKGROUND ART

An injection syringe prior to having an injection needle mounted thereto includes a syringe barrel (cylindrical tube) made from glass or plastic, a movable plunger rod (plunger), a gasket that is attached at a front end portion of the plunger rod, and a top cap attached to a needle mount part of the syringe barrel.

For the gasket, a vulcanized rubber (butyl rubber) has been conventionally used in order to prevent leakage of an injection solution.

All elastomers, including butyl rubbers and silicone rubbers that are the subject of the present invention, have been considered to not have slidability with respect to a contacting object.

Thus, gasket main bodies having a concaved groove were actually manufactured by using materials shown in Table 1, and a sliding resistance of each rubber was measured by performing a later described sliding test after various types of rubber rings were fitted onto the concaved groove.

The rubber gaskets were manufactured to have a length of 2 mm and to be larger than the internal diameter of the syringe barrel by 0.2 mm. The test was performed such that only the sliding resistance of a rubber ring was sensed by preventing the gasket main body from making contact with the inner circumferential surface of the syringe barrel.

As a result, as shown in Table 1, butyl rubber did not slide and other rubbers showed a sliding resistance not smaller than 20 N.

When performing an injection with such a large sliding resistance, if a physician or a nurse is to manually push a plunger rod of an injection syringe, he or she cannot smoothly push the plunger rod.

The requirement for achieving that is a sliding resistance not larger than 8 N at maximum.

In addition, even when an injection syringe is to be mounted on an injection device and a plunger rod of the injection syringe is to be mechanically pushed by the injection device, the plunger rod swill not move smoothly when the sliding resistance is not smaller than 20 N.

Even when mechanical pushing is to be performed by using the injection device, a sliding resistance of not larger than 15 N is required.

Thus, in order to improve inferior slidability of such rubber gaskets with respect to the inner circumferential surface of the syringe barrel, a silicone grease has been conventionally applied on the surface of the gasket and the inner circumferential surface of the syringe barrel. The applied amount of the silicone grease is, for example, not more than 8.0 mg with respect to a syringe barrel having a capacity of 5 cc.

When the silicone grease is applied, the sliding resistance becomes dramatically lower, as low as 5 to 8 N (see Table 1).

TABLE 1

Unit: Newton

| Elastomer type | Sliding resistance Silicone grease coating absent | Sliding resistance Silicone grease coating present |
|---|---|---|
| Butyl rubber | No slide movement | 5 to 8 N |
| Nitrile rubber | Not smaller than 20 N | 5 to 8 N |
| Urethane rubber | Not smaller than 20 N | 5 to 8 N |
| Fluoro rubber | Not smaller than 20 N | 5 to 8 N |
| Silicone rubber | Not smaller than 20 N | 5 to 8 N |
| Ethylene propylene rubber | Not smaller than 20 N | 5 to 8 N |
| Polyisoprene rubber | Not smaller than 20 N | 5 to 8 N |
| Polybutadiene rubber | Not smaller than 20 N | 5 to 8 N |
| Chloroprene rubber | Not smaller than 20 N | 5 to 8 N |
| Elastomer (A) of present invention | 9 to 11 N | (Ultrahigh molecular weight PE alone) |
| Elastomer (B) of present invention | 4 to 8 N | (Ultrahigh molecular weight PE + oil) |

Table 1 is a comparison of sliding resistances of various types of elastomers and medical silicone rubbers according to the present invention.

The silicone grease has a dramatic effect for improving the sliding resistance of a rubber gasket with respect to the inner circumferential surface of a syringe barrel.

However, when the silicone grease is applied on the surface of the rubber gasket or the inner circumferential surface of the syringe barrel as described above, the silicone grease directly touches a drug solution inside the syringe barrel. The results, which have been conventionally regarded as problems, are a change in quality caused by the silicone grease reacting with an active ingredient in the drug solution, fine particle contamination of the drug solution with silicon fine particles separated from the silicone grease, and adverse effects to a human body as a result.

In addition, there has been a fear of elution of soluble components contained in the rubber into the drug solution.

In particular, since pre-filled syringes, which have been used more frequently in recent years, are filled with a drug solution in advance, stored over a long period of time, and used under various environments; gaskets of the pre-filled syringes are required to have higher performance than those for ordinary injection syringes.

Examples of capabilities that are required include: (a) the gasket does not change the quality of a drug solution even when being in contact with the drug solution for a long period of time, and can be used safely; (b) ability to ensure a tight seal (liquid leakage-less property of preventing leakage of a drug solution from between the gasket and the syringe, and vapor impermeability of preventing external permeation of water content of the drug solution passed the gasket) with respect to a highly permeable drug solution; and (c) having a slidability equivalent to that of an ordinary injection syringe (the sliding resistance being not larger than 8 N when the plunger rod of the injection syringe is to be manually pushed, and not larger than 15 N when the plunger rod of the injection syringe is to be mechanically pushed with an injection device); etc.

In addition, a pre-filled syringe, which is stored for a long period of time, has been reported with a problem regarding difficulty when being used because the gasket adheres to the inner wall of the syringe barrel when the gasket is kept at a single position and has a tendency to fix to that position to cause an increase in initial motion pressure when an injection is to be performed.

Thus, in an attempt to solve the problem, Patent Literature 1 proposes, as a slidability improvement measure, a combination between a thermoplastic or thermosetting elastic elastomer having a Shore A hardness of 30 to 80 (ordinarily 40 to 50 when butyl rubber is used) and a rigid plastic material (hereinafter, simply referred to as a rigid plastic) such as a medical grade polypropylene having excellent chemical resistance.

More specifically, a proposed gasket is obtained by creating cores having various shapes with an outer diameter that is smaller than the internal diameter of a syringe barrel by using a rigid plastic, and fitting, onto the cores, a ring-shaped elastomeric sleeve made from an elastomer and having "rubber elasticity" for preventing leakage of liquid.

As another example, Patent Literature 2 discloses a gasket formed entirely of a slidable silicone rubber obtained by loading a silicone rubber with a silicone oil and a polyethylene powder, and vulcanizing and molding the silicone rubber.

CITATION LIST

Patent Literature

[PTL 1] Japanese Laid-Open Patent Publication (translation of PCT application) No. 2009-505794 (paragraph number: 0012)
[PTL 2] Japanese Laid-Open Patent Publication No. 05-131029 (paragraph number: 0008-0015)

SUMMARY OF THE INVENTION

Problems to be Solved by the Invention

However, as described above, almost all hitherto known elastomers, although having "rubber elasticity", have an extremely high "sliding resistance" with respect to a contacting object.

In other words, since an elastomer displaying high "slidability" without using silicone grease that dramatically improves slidability has not been commonly known at the present time; always applying the silicone grease on the inner circumferential surface of a syringe has been considered essential for obtaining a slidability suitable for practical use.

Thus, a contact between silicone grease and an injection solution is actually unavoidable in the injection syringe described in Patent Literature 1.

On the other hand, as in Patent Literature 2, although a gasket formed entirely of a slidable silicone rubber has been disclosed, the added silicone oil, even if the amount is small, cannot be prevented from exuding to the surface of the gasket to make contact with, and contaminate, the loaded injection solution.

Even if the slidable silicone rubber of the cited literature 2 is applied to the elastomeric sleeve of the cited literature 1, a liquid-contact side flanged end of the core of the cited literature 1 is slenderer than the outer diameter of the elastomeric sleeve and forms a gap from the inner circumferential surface of the syringe barrel. Even when the elastomeric sleeve is press-fitted to the syringe barrel, the gap still exists between the inner circumferential surface of the syringe barrel and the liquid-contact side flanged end of the core. There is the fear of the loaded drug solution entering the gap, making contact with the elastomeric sleeve, and making contact with a silicone oil that has bled (exuded) to the surface of the elastomeric sleeve to cause contamination of the loaded drug solution.

Thus, in order to solve the above described problem, the inventors use a medical grade rigid plastic such as PTFE (polytetrafluoroethylene) for a "gasket main body" that makes a direct contact with the injection solution, and use a "slidable silicone rubber" for a "slide-contact ring" that does not make contact with the injection solution.

A first objective of the present invention is to obtain a groundbreaking gasket that is highly safe and provides a highly tight seal over a long period of time, and that has, with respect to a syringe barrel of the gasket, a small sliding resistance, for example, a sliding resistance not larger than 8 N when a plunger rod of an injection syringe is to be manually pushed or a sliding resistance not larger than 15 N for mechanical pushing by using an injection device.

A second objective of the present invention is to obtain a syringe having the above described characteristics by using the gasket that has sufficiently satisfactory "slidability" without making a compromise in "rubber elasticity", considered to be opposite thereof, for ensuring "sealability (water tightness)" and that also has high "vapor impermeability".

Solution to the Problems

Claim 1 is directed to a gasket 10 that is to be press-fitted in a syringe barrel 1 and used in a slidable manner,
the gasket 10 including: a main body portion 26 that is formed of a rigid plastic having a drug solution-resistant property against a drug solution 30 to be loaded in the syringe barrel 1, and that has a slide-contact surface 11 that slidingly contacts an inner circumferential surface 2 of the syringe barrel 1; and a slide-contact ring 19 that is fitted in a concaved groove 18 formed over a whole circumference of the slide-contact surface 11, and is configured to slidingly contact the inner circumferential surface 2 of the syringe barrel 1, wherein
within the slide-contact surface 11, at least a slide-contact surface 11a adjacent to a liquid contact surface 14 with respect to the drug solution 30 is formed to be liquid-tight with respect to the inner circumferential surface 2,
the slide-contact ring 19 is formed of a slidable silicone rubber G obtained by adding a spherical ultrahigh molecular weight polyethylene fine powder to a silicone rubber base material 19c, and the slidable silicone rubber G contains, in volume ratio, the ultrahigh molecular weight polyethylene fine powder by 44.5 to 60% and the silicone rubber base material 19c for the remaining portion.

Claim 2 is directed to the gasket 10 according to claim 1, wherein a silicone oil is additionally added to the slidable silicone rubber G of the slide-contact ring 19, and the slidable silicone rubber G contains, in volume ratio, the ultrahigh molecular weight polyethylene fine powder by 30 to 65%, the silicone oil by 7 to 40%, and, with respect to a total of the ultrahigh molecular weight polyethylene fine powder and the silicone oil being 37 to 72%, the silicone rubber base material 19c for the remaining portion.

The "medical slidable silicone rubber G" which is a cured body used as "the slide-contact ring 19" of claim 1 or 2 is one obtained by adding the spherical ultrahigh molecular weight polyethylene fine powder to the silicone rubber base material (claim 1), or one obtained by additionally adding thereto the silicone oil (claim 2).

The ultrahigh molecular weight polyethylene fine particles in the form of a fine powder added to the medical slidable silicone rubber G are schematically shown in (A) and (B) of FIG. 5. In the figure, the ultrahigh molecular weight polyethylene fine particles are represented with reference character "19a", and a silicone rubber base material connecting the ultrahigh molecular weight polyethylene fine particles 19a is represented as "19c". In (B) of FIG. 5, the silicone oil thinly adhered to the surfaces of the ultrahigh molecular weight polyethylene fine particles 19a is represented with reference character "19b".

The spherical ultrahigh molecular weight polyethylene fine powder has, for example, an average molecular weight of $1 \times 10^6$ to $7 \times 10^6$, does not have water permeability, sticks to almost nothing, and does not melt even at a high temperature. The spherical form is maintained even when the medical slidable silicone rubber G having the spherical ultrahigh molecular weight polyethylene fine powder added thereto is molded with high pressure.

A liquid, greasy, or clayish organopolysiloxane in which an organic functional group (vinyl group, etc.) is incorporated and whose main chain is formed of silicon-oxygen is used as the material of the slidable silicone rubber G.

Then, the material is being added with required additives, kneaded, and polymerized to reach a target molecular weight to obtain the slidable silicone rubber G. Obviously, the slidable silicone rubber G, not just the slidable silicone rubber G but any polymer, contains a very small amount of a material having a small molecular weight (referred to as an oligomer). However, by itself, a conventional silicone rubber having a high molecular weight has a sliding resistance not smaller than 20 N as shown in Table 1 and does not show slidability.

With respect to such general technical common knowledge, claim 1 of the present invention focuses on this "residual oligomer", and causes this "residual oligomer" to play a role as a "silicone oil" since the spherical ultrahigh molecular weight polyethylene fine powder is added. More specifically, by forming a thin "oligomer coating film" around the spherical ultrahigh molecular weight fine particles 19a, rotation action is generated in the spherical ultrahigh molecular weight fine particles 19a, and the sliding resistance of the slidable silicone rubber G can be reduced to a practical use range (9 to 11 N) applicable for a gasket (Table 1).

The invention according to claim 2 is directed toward further adding, to the configuration of claim 1, a silicone oil by a required amount. Since the amount of the "oligomer" in claim 1 is very small, improvement of slidability is naturally limited.

By actively adding the silicone oil, the "slidability" of the medical silicone rubber G according to the present invention is dramatically increased to (4 to 8 N) (Table 1).

(B) of FIG. 5 is a schematic diagram of a case in which the silicone oil is added as described above, and, in the figure, an added silicone oil film 19b adheres around the ultrahigh molecular weight polyethylene fine particles 19a to create a structure in which the silicone rubber base material 19c fills the intervals between the ultrahigh molecular weight polyethylene fine particles 19a.

Both in claims 1 and 2, the silicone rubber base material 19c loses the function as a connection when the added amount of the ultrahigh molecular weight polyethylene fine particles 19a is excessive. On the other hand, when the added amount is too small, most of the ultrahigh molecular weight polyethylene fine particles 19a are taken within the silicone rubber base material 19c, and "slidability" cannot be obtained. The preferable range will be described later.

It should be noted that, in claim 2, the silicone oil to be added ranges from those having a low viscosity (e.g., those with about 1000 cP) to those having a high viscosity (e.g., those with about 100,000 cP or higher) referred to as grease (Table 2).

The viscosity of the silicone oil contributes in the improvement in slidability to some degree, but not to a degree of a "ball bearing effect" by the ultrahigh molecular weight polyethylene fine powder.

The invention according to claim 3 relates to the ultrahigh molecular weight polyethylene fine powder according to claim 1 or 2, wherein the range of the particle sizes of the ultrahigh molecular weight polyethylene fine particles 19a is from 10 to 300 μm (Table 2). Further preferably, the range is from 20 to 50 μm. Having particles with a too-large particle size of not smaller than 300 μm rather impairs sealability.

The used ultrahigh molecular weight polyethylene fine powder is, for example, an ultrahigh molecular weight material having an average molecular weight of $1 \times 10^6$ to $7 \times 10^6$.

The fine particles 19a of the ultrahigh molecular weight polyethylene fine powder are spherical with various sizes as described above, have fine concavities and convexities on the surfaces, and have adhered thereto thin films of the added silicone oil and the oligomer remaining in the silicone rubber base material 19c.

The ultrahigh molecular weight polyethylene fine particles 19a having a molecular weight of 1,000,000 to 3,000,000 or up to 7,000,000 do not have water permeability, stick to almost nothing, do not melt even at a high temperature, and maintain the spherical form even when being molded with high pressure.

It should be noted that since the range of the particle sizes of the ultrahigh molecular weight polyethylene fine particles 19a is as broad as 10 to 300 μm, small particles enter and fill the gaps between large particles to increase the degree of filling of the ultrahigh molecular weight polyethylene fine particles 19a.

As a result, the silicone rubber G of the present invention has significantly improved impermeability compared to a conventional water-permeable silicone rubber to which a filler such as a fine-particle silica is added.

Table 2 is a formulation table of the slidable silicone rubber G used for the slide-contact ring 19 of the present invention, and the unit of the numbers therein is ml (milliliter).

The gasket main body 26 was manufactured so as not to slidingly contact the syringe barrel inner circumference surface 2 as described above, and the slide-contact ring 19 having the formulation as shown in Table 2 was fitted thereon to measure the sliding resistance of the slide-contact ring 19 alone.

The sliding resistance of the slide-contact ring 19 alone is almost the same between a later described peroxide curing type slidable silicone rubber and an addition reaction-type cured slidable silicone rubber, or is slightly better in the addition reaction-type silicone rubber.

TABLE 2

| | | Ultra high molecular weight spherical PE + silicone oil (PE + oil) Sample number | | | | | | | | | |
|---|---|---|---|---|---|---|---|---|---|---|---|
| | | No. 1 Example 1 | No. 2 Exmple 2 | No. 3 Example 3 | No. 4 Example 4 | No. 5 Example 5 | No. 6 Example 6 | No. 7 Example 7 | No. 8 Example 8 | No. 9 Example 9 | No. 10 Example 10 |
| Average sliding resistance (unit = N) | | 7.1 | 6.9 | 6.6 | 5.5 | 5.7 | 4.0 | 5.0 | 5.4 | 4.7 | 7.0 |
| Material Polysiloxane | | 29.9 | 29.9 | 29.9 | 29.9 | 29.9 | 29.9 | 29.9 | 29.9 | 29.9 | 29.9 |
| Silica powder | | 5.5 | 5.5 | 5.5 | 5.5 | 5.5 | 5.5 | 5.5 | 5.5 | 5.5 | 5.5 |
| Ultrahigh molecular weight spherical polyethylene | Particle size 10 to 300 μm | 27.5 | 56.4 | 56.4 | 56.4 | 56.4 | 56.4 | 56.4 | 56.4 | 31.4 | 45.2 |
| Silicone oil (cP) | 50000 | 5.4 | | 10.3 | 20.6 | 30.9 | | | | | |
| | 12500 | | | | | | | 30.9 | | | |
| | 3000 | | | | | | | | 30.9 | | |
| | 1000 | | 10.3 | | | | 30.9 | | | 30.9 | 30.9 |
| Total | | 68.3 | 102.1 | 102.1 | 112.4 | 122.7 | 122.7 | 122.7 | 122.7 | 97.7 | 111.5 |
| Ultrahigh molecular weight spherical PE (30 to 65%) | Volume ratio (%) | 40.3 | 55.2 | 55.2 | 50.2 | 46.0 | 46.0 | 46.0 | 46.0 | 32.1 | 40.5 |
| Silicone oil (0 to 40%) | Volume ratio (%) | 7.9 | 10.1 | 10.1 | 18.3 | 25.2 | 25.2 | 25.2 | 25.2 | 31.6 | 27.7 |
| | | 48.2 | 65.3 | 65.3 | 68.5 | 71.1 | 71.1 | 71.1 | 71.1 | 63.8 | 68.3 |

| | | Ultra high molecular weight spherical PE (no silicone oil) Sample number | | | | | PE + oil | |
|---|---|---|---|---|---|---|---|---|
| | | No. 11 Example 11 | No. 12 Example 12 | No. 13 Example 13 | No. 14 Comparative Example 1 | No. 15 Comparative Example 2 | No. 16 Comparative Example 3 | No. 17 Comparative Example 4 |
| Average sliding resistance (unit = N) | | 10.3 | 9.3 | 10.5 | 17.3 | — | — | — |
| Material Polysiloxane | | 29.9 | 29.9 | 29.9 | 29.9 | 29.9 | 29.9 | 29.9 |
| Silica powder | | 5.5 | 5.5 | 5.5 | 5.5 | 5.5 | 5.5 | 5.5 |
| Ultrahigh molecular weight spherical polyethylene | Particle size 10 to 300 μm | 28.4 | 50.2 | 51.8 | 27.3 | 60.1 | 25.8 | 95.4 |
| Silicone oil (cP) | 50000 | | | | | | | |
| | 12500 | | | | | | | |
| | 3000 | | | | | | | |
| | 1000 | | | | | | 42.5 | 5.9 |
| Total | | 63.8 | 85.6 | 87.2 | 62.7 | 95.5 | 103.7 | 136.7 |
| Ultrahigh molecular weight spherical PE (30 to 65%) | Volume ratio (%) | 44.5 | 58.6 | 59.4 | 43.5 | 62.9 | 24.9 | 68.9 |
| Silicone oil (0 to 40%) | Volume ratio (%) | 0.0 | 0.0 | 0.0 | 0.0 | 0.0 | 41.0 | 4.3 |
| | | 44.5 | 58.6 | 59.4 | 43.5 | 62.9 | 65.9 | 74.1 |

Table 2 is the formulation table of the silicone rubber and a table comparing the sliding resistances thereof.

When Silicone Oil is not Added and Only Function of Oligomer is Relied Upon (Nos. 11 to 15).

When the ultrahigh molecular weight polyethylene fine powder was contained by 43.5 vol % (Comparative Example 1), an average sliding resistance thereof was 17.3 N, and when the ultrahigh molecular weight polyethylene fine powder was contained by not more than 43.5 vol %, the ultrahigh molecular weight polyethylene fine powder cannot be used since the sliding resistance thereof exceeds the target value of 15 N for mechanical pushing.

On the other hand, when the ultrahigh molecular weight polyethylene fine powders (Examples 11 to 13) were each contained by not less than 44.5 vol %, average sliding resistances thereof were respectively 10.3 N, 9.3 N, and 10.5 N, and in this case, the ultrahigh molecular weight polyethylene fine powders can be used for mechanical pushing since the target value of not larger than 15 N for mechanical pushing is satisfied. From the results above, when only the function of the oligomer is to be relied upon without adding the silicone oil, the ultrahigh molecular weight polyethylene fine powder has to be contained by not less than 44 vol %.

On the other hand, when the ultrahigh molecular weight polyethylene fine powder was contained by 62.9 vol % in the case of not adding the silicone oil (Comparative Example 2), a large amount of the silicone rubber base material cannot be added, a kneaded object kneaded in a kneader (kneading machine) loses viscosity, and the function as a connection for the silicone rubber base material is lost.

Thus, when the silicone oil is not added, the added amount of the ultrahigh molecular weight polyethylene fine powder is 44 to 60 vol % (preferably 45 to 55 vol %).

When Silicone Oil is Added (Nos. 1 to 10, 16, 17)

In this case, although depending on the added amount of the silicone oil, when the ultrahigh molecular weight polyethylene fine powder was contained by not more than 24.9 vol % (Comparative Example 3), the amount of the ultrahigh molecular weight polyethylene fine powder was too small and improvement in the sliding resistance was insufficient.

Conversely, when the ultrahigh molecular weight polyethylene fine powder was contained by 68.9 vol %, the added amounts of the silicone rubber base material (26.8 vol %) and the silicone oil (4.3 vol %) were too small, and, also in this case, a kneaded object kneaded in a kneader (kneading machine) loses viscosity and the function as a connection for the silicone rubber base material is compromised.

On the other hand, when the ultrahigh molecular weight polyethylene fine powder was contained by not less than 32.1 vol %, the remainder was the silicone oil (31.6 vol %) and the silicone rubber base material (36.3 vol %) (Example 9), and the average sliding resistance was lowered to 4.7 N, showing a sliding resistance also applicable for manual pushing (Example 9).

Thus, the ultrahigh molecular weight polyethylene fine powder, when being contained by not less than 30 vol %, emerges on the surface of the silicone rubber G, acts as a lubrication main agent, and sufficiently plays a role as a later described "ball bearing". The upper limit of the ultrahigh molecular weight polyethylene fine powder is 65 vol %. More specifically, the added amount of the ultrahigh molecular weight polyethylene fine powder is from 30 to 65 vol %.

As described above, when the silicone oil is not added, the oligomer or the silicone oil forms a thin film on the surfaces of the ultrahigh molecular weight polyethylene fine particles 19a and functions as a lubrication assistant for assisting rotation of the ultrahigh molecular weight polyethylene fine particles 19a described later.

Since the residual amount of the oligomer is very small, the function of the oligomer as a lubrication assistant is smaller compared to when the silicone oil is actively added.

On the other hand, by actively adding the silicone oil, the sliding resistance gradually reduces.

However, when the silicone oil is to be added, adding 40 vol % or more does not particularly increase the sliding resistance but rather compromises processability and results in many ill effects (Comparative Example 3).

Based on Examples 1 to 10 in Table 2, the preferable range of the silicone oil for actively improving slidability is 7 to 40 vol % (the more preferable range to obtain a sliding resistance of not larger than 7 N is 10 to 30 vol %).

When the slide-contact ring 19 is obtained through molding with a metal mold, the preferable ranges are 40 to 65 vol % (more preferable range is 45 to 55 vol %) for the ultrahigh molecular weight PE fine powder, and 7 to 40 vol % (more preferable range is 10 to 30 vol %) for the silicone oil (see Examples 1 to 10 in Table 2).

The ultrahigh molecular weight PE fine powder and the silicone oil are contained within the ranges described above, and, with respect to the total of the ultrahigh molecular weight polyethylene fine powder and the silicone oil being 37 to 72% in volume ratio, the silicone rubber base material is contained by the remaining portion. It should be noted that although the total of the ultrahigh molecular weight polyethylene fine powder and the silicone oil is 65.9 vol % in Comparative Example 3 and is within the range, the ultrahigh molecular weight polyethylene fine powder and the silicone oil are respectively contained by 24.9 vol % and 41.0 vol %, which are both outside the ranges.

1 The invention according to claim 4 (addition reaction-type slidable silicone rubber G) relates to the material (or raw material) of the silicone rubber base material 19c according to claim 1 or 2, wherein the material is obtained by thermally curing an amorphous polysiloxane having a vinyl group incorporated in a molecule thereof and an amorphous polysiloxane having a reactive hydrogen incorporated at a molecule terminal thereof, through a reaction using, as a catalyst, any one of platinum, rhodium, or an organic compound of tin.

The invention according to claim 5 (peroxide cross-linking type slidable silicone rubber G) relates to the material (or raw material) of the silicone rubber base material 19c according to claim 1 or 2, wherein the material is obtained through a curing reaction of a polysiloxane having a vinyl group incorporated therein by using a peroxide as a curing catalyst.

The invention according to claim 6 relates to a filler to be added to, and formed with, the liquid or greasy (i.e., amorphous) silicone rubber base material, and used plasticity-level adjustment. As the filler, a filler including a fine-particle silica as a main component and at least one of a PTFE fine powder, glass beads, talc, a titanium powder, or carbon, is added. The particle size of the fine-particle silica is preferably from 0.05 to 2 μm. In addition, a pigment is added as a coloring agent if necessary.

Although the amorphous polysiloxane as described above is used as the material (raw material) of the silicone rubber base material 19c; for the purpose of setting the plasticity level thereof to, for example, 100 to 500, filling objects such as the fine powder silica and the like are added or the degree of polymerization is adjusted. In a polymer, a very small portion of the material remains as an oligomer. One obtained by adding the above described filler to the material is the silicone rubber base material 19c that becomes the raw material of the silicone rubber G of the present invention.

The invention according to claim 7 with respect to the gasket 10 according to any one of claims 1 to 6 has a feature in which the molded slide-contact ring 19 is heated (annealed) at a temperature not higher than 130° C. for 4 to 24 hours (preferably, at 120 to 130° C. for 4 to 10 hours).

As a result of the heating (annealing), anti-creep properties at 40° C. for an addition reaction-type silicone rubber significantly improve, permanent deformation is less likely to appear even when being maintained at the high temperature described above for a long period of time, and leakage of liquid does not occur when the slide-contact ring 19 is formed.

The invention according to claim 8 relates to the slide-contact surface 11a of the gasket 10 according to any one of claims 1 to 2, wherein a width S (i.e., seal width S) of the slide-contact surface 11a is 0.1 to 2 mm (further preferably within a range of 0.2 to 1.5 mm).

When the thickness S of the slide-contact surface 11a is not larger than 0.1 mm, leakage of the drug solution 30 may occur as a result of insufficient strength because of being too thin. When the thickness (seal width) S of the slide-contact surface 11a is 3 mm and a diameter difference for press-fitting is 150 μm, cracks may occur if the syringe barrel 1 is made of a cycloolefin resin (COP).

For the purpose of safety and setting the sliding resistance to be not larger than 15 N, the maximum thickness of the seal width S of the slide-contact surface 11a is set to 2 mm. When the seal width S is within a range from 0.1 to 0.6 mm, a liquid-contact side sliding part 16 is pressed against the syringe barrel inner circumference surface 2 and largely bends at the edge.

On the other hand, when the seal width S is larger than 0.6 mm and up to 2 mm, the slide-contact surface 11a makes contact with the syringe barrel inner circumference surface 2 and stops water since the liquid-contact side sliding part 16 has a certain level of strength.

The invention according to claim 9 has a feature in which the main body portion 26 of the gasket 10 according to any one of claims 1 to 2 is a closed-cell PTFE.

In a closed-cell PTFE obtained with a hot isostatic pressing method, ultrafine gaps existing between particles of the PTFE formed through sintering are blocked with certainty.

As a result, in a case where this PTFE is used for formation, when the gasket 10 is used for a pre-filled syringe A that is stored for an extended period of time while being filled with the drug solution 30, leakage of the drug solution 30 from the ultrafine gaps during storage can be prevented with certainty.

The invention according to claim 10 relates to a syringe A (FIG. 1) having a feature of "including the syringe barrel 1 to be filled with the drug solution 30, the gasket 10, according to any one of claims 1 to 9, that is press-fitted inside the syringe barrel 1, and a plunger rod 5 mounted in the gasket 10".

Examples of the syringe A includes a pre-filled syringe and an ordinary disposable syringe (refers to a general injection syringe that is not filled with a drug solution and is used by suctioning the drug solution from an injection needle at the time of injection).

Since the gasket 10 used here has "high slidability" and "sealability" as described above, and vapor impermeability is extremely superior in the slide-contact ring 19 formed of the silicone rubber G according to the present invention and also, needless to say, in the resin forming the main body portion 26 as shown in FIGS. 1 and 2; even when the syringe is stored for an extended period of time while being filled with the drug solution 30 as the pre-filled syringe A, penetration of vapor through the gasket 10 was not observed almost completely. In addition, since the amount of leakage of the silicone oil added to the slide-contact ring 19 of the gasket 10 to the surface is extremely small; even when the gasket 10 is moved back and forth within the syringe barrel 1, the silicone oil that has leaked out from the slide-contact ring 19 does not adhere to the inner surface of the syringe barrel 1 almost completely.

Thus, the gasket 10 can be used not only for the pre-filled syringe as described above, but also for an ordinary disposable syringe.

Advantageous Effects of the Invention

As can be understood from above, with the gasket 10 according to the present invention, by using a rigid plastic such as PTFE for the gasket main body and by using a "slidable silicone rubber" at a portion that does not make contact with an injection solution, an injection syringe and a gasket having the demanded capability can be obtained, and, in particular, a pre-filled syringe can be obtained.

DESCRIPTION OF EMBODIMENTS

Figure 1:
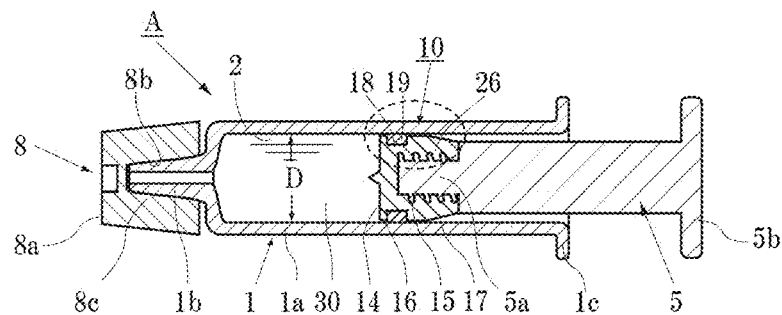
FIG. 1 is a cross sectional view of a pre-filled syringe to which the present invention is applied.

In the following, the present invention will be described in accordance with illustrated examples. FIG. 1 is a cross sectional view of the pre-filled syringe A to which the gasket 10 of the present invention is applied.

Although not diagrammatically represented, the gasket of the present invention can also be applied to an ordinary disposable syringe.

In the following, the pre-filled syringe A will be described as a representative example.

Figure 2A:
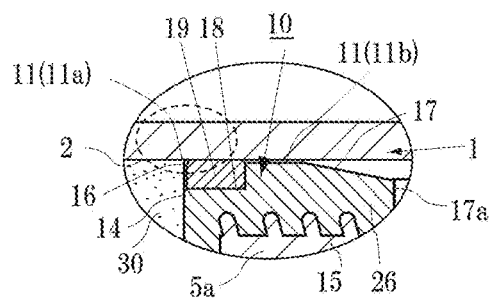
In FIG. 2, (A) and (B) are each an enlarged cross sectional view of a portion shown with an ellipse drawn by a broken line in FIG. 1.
Figure 2B:
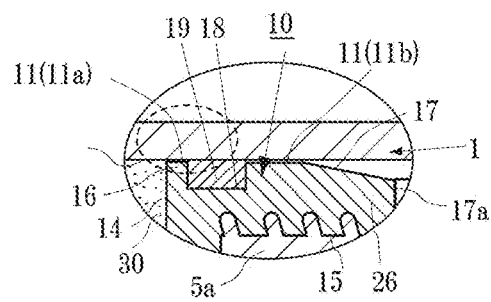
Figure 3A:
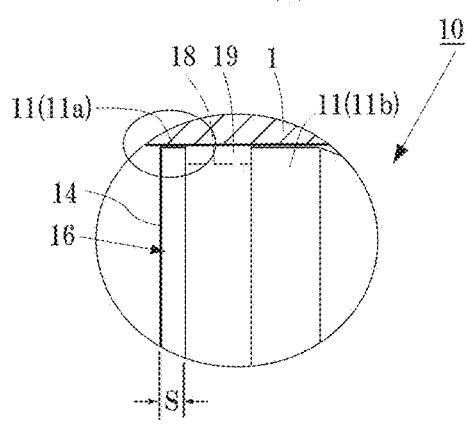
In FIG. 3, (A) is an enlarged front view showing the portion shown with the ellipse drawn by the broken line in FIG. 1, and (B), (C), and (D) are drawings showing the outer shape of the slide-contact ring.
Figure 3B:
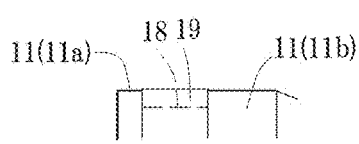
Figure 3C:
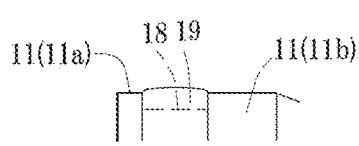
Figure 3D:
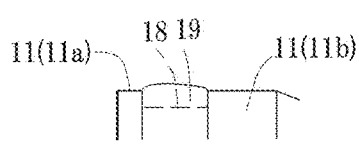

As shown in FIG. 1, the pre-filled syringe A includes the gasket 10, the syringe barrel 1 filled with the drug solution 30, the plunger rod 5 to be mounted in the gasket 10, and a top cap 8. In the present specification, common members are indicated with the same reference character. In FIG. 2 and further, the description of overlapping portions that already have been provided are to be cited and description thereof is omitted in principle to prevent the description from being complicated.

The syringe barrel 1 is a cylindrical container. A mount part 1b on which an injection needle that is not shown is mounted is disposed at the front end of a barrel main body 1a in a protruding manner, and a flange 1c for finger placement is formed on the back end. For the material of the syringe barrel 1, a hard resin (e.g., cycloolefin resin (hereinafter, referred to as COP)), polypropylene (hereinafter, referred to as PP), or an ethylene-norbornene copolymer (hereinafter, referred to as COC), etc., is used. When the seal width S (described later) of the gasket main body 26 is 0.1 to 0.6 mm (preferably 0.1 to 0.3 mm), a glass syringe barrel 1 can also be used since the glass syringe barrel 1 fits nicely with the syringe barrel inner circumference surface 2.

The plunger rod 5 is a rod shaped member having a male-screw part 5a formed at the front end part and a finger rest part 5b formed at the back end. On the outer circumferential surface of the male-screw part 5a of the plunger rod 5, male-screw threads to be screwed in a female-screw hole 15 of the gasket main body 26 are engraved. The material of the plunger rod 5 is formed of a resin and the like such as cyclic polyolefin, polycarbonate, and polypropylene.

The top cap 8 is attached to the needle mount part 1b of the syringe barrel 1, and is a sealing member to prevent leakage of the drug solution 30 loaded in the syringe barrel 1 and contamination of the drug solution 30 by unwanted germs drifting in air. The top cap 8 includes a cap main body 8a having a circular truncated cone shape, and an engagement protrusion 8c extending in an opening direction from a top surface of the cap main body 8a and having formed thereon a concaved portion 8b in which the needle mount part 1b is fitted. The top cap 8 is formed from an elastomer having a drug solution-resistant film (PTFE or PFA) layered on the inner circumferential surface thereof. Examples of the elastomer include "vulcanized rubber", "thermosetting elastomer", and "thermoplastic elastomer".

The entirety of the main body portion 26 (alternatively, also referred to as the gasket main body 26) of the gasket 10 shown in FIG. 1 is formed of a hard material (rigid plastic having drug solution-resistant property) that does not react with the drug solution 30, such as PTFE, PFA (tetrafluoroethylene-perfluoroalkyl vinyl ether copolymer), FEP (a copolymer of ethylene tetrafluoride and propylene hexafluoride), PCTFE (polychlorotrifluoroethylene), PVDF (polyvinylidene fluoride), polypropylene (PP), polyethylene including ultrahigh molecular weight polyethylene, COP, COC, or fluorine resin.

Although the PTFE used in the present invention may be pure PTFE, it is more preferable to use, since the main body portion 26 of the gasket 10 becomes elastic, a modified object having mixed therein, for example, 1 to 15 mass % of a fluorine resin such as a tetrafluoroethylene-hexafluoropropylene copolymer, and a polytetrafluoroethylene-perfluoroalkyl vinyl ether copolymer (abbreviated name: PFA) which are crystallization inhibitors of PTFE.

As the PTFE used in the present invention, a block (round bar material) closed-celled by a hot isostatic pressing method that is called HIP treatment is used in addition to the pure PTFE or the modified object of PTFE.

A PTFE primary sintered block is obtained by compression molding and then sintering a pure PTFE powder or a powder of the modified object of PTFE. In the sintering, although powders in contact within each other are attached firmly, extremely fine gaps are formed at non-contact portions as a whole, and are connected to allow a minute amount of fluid to pass through.

When the PTFE primary sintered block is hot-isotropic pressed, the PTFE primary sintered block is compressed, and the ultrafine gaps existing between particles of PTFE are closed with certainty to form closed-cells. Performing the hot isotropic pressing under reduced pressure is more effective.

Next, the shape of the gasket 10 in FIG. 1 will be described. The main body portion 26 of the gasket 10 is columnar, and is formed with, on the back end surface thereof, the female-screw hole 15 on which the plunger rod 5 is to be mounted. At the slide-contact surface 11 where the outer circumferential surface of the front end side of the main body portion 26 slidingly contacts the inner circumferential surface 2 of the syringe barrel 1, a portion 17 extending from the back end surface of the slide-contact surface 11 to a plunger rod mounting surface 17a is tapered such that the diameter gradually decreases. This portion is referred to as a tapered portion 17. The material of the main body portion 26 is as described above.

A shallow concaved groove 18 is formed over the whole circumference of the mid-portion of the slide-contact surface 11 of the main body portion 26.

In other words, the narrow slide-contact surfaces 11a and 11b exist on both sides of the concaved groove 18. Both the slide-contact surfaces 11a and 11b preferably have liquid-tightness, and at least the slide-contact surface 11a adjacent to the liquid contact surface 14 with respect to the drug solution 30 is formed to have liquid-tightness.

Thus, the portion (the liquid-contact side sliding part 16) having the slide-contact surface 11a is press-fitted to the syringe barrel 1 with a press-fit margin described later.

On the concaved groove 18, the slide-contact ring 19 that slidingly contacts the inner circumferential surface 2 of the syringe barrel 1 is fitted. The slide-contact surface 11a will be described later.

"The slidable silicone rubber G" that forms the slide-contact ring 19 is a slidable elastomer as described above, and is a thermosetting resin used as one example of the silicone rubber material.

Two types thereof exist, and one example thereof is a liquid or greasy "organopolysiloxane" which is the raw material, and is a material having a methyl group, a vinyl group, a phenyl group, or a trifluoropropyl group incorporated in a molecule thereof depending on a demanded special characteristic.

Although any of those described above may be used in the present invention, one example is a rubbery peroxide cross-linking type silicone rubber obtained by using a liquid or greasy "organopolysiloxane" having a vinyl group incorporated therein, adding a required filling object and a peroxide curing agent, kneading the mixture, and curing the mixture to reach a target molecular weight.

Another example is an addition reaction-type silicone rubber obtained by heating and curing a clayish polysiloxane having a vinyl group incorporated in the molecular thereof and a clayish polysiloxane having a reactive hydrogen incorporated at the molecule terminal thereof, through a reaction using platinum or rhodium, or an organic compound of tin as a catalyst. This addition reaction-type silicone rubber displays a further superior creep resistance characteristic when compared to the peroxide cross-linking type silicone rubber.

When a "thermoplastic elastomer" is used for a slide-contact ring for the gasket instead of "the slidable silicone rubber G" which is a "thermosetting resin"; creep deformation possibly occurs on the slide-contact ring by compressive deformation when being stored while being confined within the syringe barrel for an extended period of time, resulting in leakage of liquid and poor sliding to become unsuited for medical use.

Regarding this point, the slidable silicone rubber G which is a "thermosetting resin" does not undergo creep deformation when compared to a "thermoplastic elastomer", and is optimal as a slide-contact ring for gaskets for medical use.

The silicone rubber base material according to the present invention is formed by adding, for example, a peroxide which is a cross-linking agent to a liquid or greasy organosiloxane which is a silicone rubber material (or adding a curing catalyst to the two types of clayish polysiloxanes), further adding, a silica fine powder by, for example, 25%, and kneading the mixture using a kneader. Then, a predetermined amount of the ultrahigh molecular weight fine powder and additionally the silicone oil are added to the silicone rubber base material 19c to obtain the slidable silicone rubber G according to the present invention.

The polyethylene resin forming the fine particles 9a in the fine powder form has an ultrahigh molecular weight.

(For example, the average molecular weight thereof reaches, in some cases, 1,000,000 to 3,000,000 or even larger up to 7,000.000.)

Such ultrahigh molecular weight particles do not have water permeability and stick to almost nothing.

Since the ultrahigh molecular weight polyethylene has such a large molecular weight, the ultrahigh molecular weight polyethylene does not melt even at a high temperature, and maintains its spherical form even when being molded with a high pressure.

The surface of the spherical ultrahigh molecular weight polyethylene is relatively smooth but some concavities and convexities are also observed.

The range of the particle sizes of the spherical ultrahigh molecular weight fine particles 19a contained in the fine powder is 10 to 300 μm (Table 2), and further preferably 20 to 50 μm.

Depending on the grade, one having an average particle size of 25 μm, 30 μm, or a size other than those is used.

When the width of the particle size distribution is large, particles having a small size enter and fill the gaps between large particles to achieve close-packing.

Since the fine particles 19a do not have water permeability when being closely packed, the medical slidable silicone rubber of the present invention shows extremely low water permeability as a whole even if a silicone oil or a silicone rubber base material having water permeability is used.

The silicone oil is added or not added to the slidable silicone rubber G of the present invention depending on the case.

When an object having the target molecular weight is obtained through polymerization as described above, obviously, a material (oligomer) having a small molecular weight remains in a very small amount.

When the silicone oil is not added, the existing ultrahigh molecular weight polyethylene fine particles 19a functions similarly to the silicone oil, and slidability is provided to the silicone rubber which fundamentally had not been considered to have slidability.

However, since the residual amount is very small, even when the ultrahigh molecular weight polyethylene fine particles 19a exist, the improvement in slidability is limited, and sliding has been shown in a range of about 9 to 11 N (Table 1).

On the other hand, when the silicone oil is added, since the kneaded silicone oil and the silicone rubber base material 19c are compatible with each other, the silicone oil, if loaded by a proper amount, uniformly disperses within the silicone rubber base material 19c and thinly exudes on the surface of the medical slidable silicone rubber G of the present invention.

In addition, based on observations described next, the silicone oil is thought to simultaneously adhere to the surface of the ultrahigh molecular weight polyethylene fine particles 19a to form the thin film 19b, and enter the concaved portions of the surface to form lubricating liquid pools to assist lubrication during rotation of the ultrahigh molecular weight polyethylene fine particles 19a.

Regarding the molding method of the slide-contact ring 19, a compression metal mold capable of molding the slide-contact ring 19 is heated to, for example, 150° C., and the above described molding material (the silicone rubber base material 19c obtained by adding and kneading the ultrahigh molecular weight PE powder and also the silicone oil) is loaded in the compression metal mold to be heated and pressurized to cause thermal cross-linking within 1 to 10 minutes to obtain the intended slide-contact ring 19.

Then, in the case with the addition reaction-type silicone rubber, by additionally heating (annealing) at 120 to 130° C. for 4 to 10 hours, the slide-contact ring 19 having the intended physical properties (anti-creep properties) is obtained.

In the case with the peroxide cross-linking type silicone rubber, the physical property improving effect by the annealing is small compared to the addition reaction-type silicone rubber, but a certain degree improvement is obtained.

An annealing temperature of 145° C. or higher has to be avoided since low molecular weight substances inside the silicone rubber G bleed (exude) to the surface of the silicone rubber G.

The outer diameter of the slide-contact ring 19 is set to be slightly larger than the outer diameter of the portion of the slide-contact surface 11a of the liquid-contact side sliding part 16 of the main body portion 26 such that a liquid-tight close adherence to the inner circumferential surface 2 of the syringe barrel 1 is obtained.

The shape of the outer circumferential surface is conceivably, for example, one in which the outer circumferential surface of the slide-contact ring 19 is linear or arched to be slightly bulged at the center, or one in which the slide-contact surface 11a side of the liquid contact surface side is slightly bulged ((B), (C), and (D) of FIG. 3).

In the linear case, the whole outer-circumference surface equally contacts the syringe barrel inner circumference surface 2, whereas when a bulge exists, the bulge portion is contacted strongly.

Since the slide-contact ring 19 elastically elongates, when the thickness and shape (as described above, linearly, gradually thickened at a groove center, and the like) of the groove bottom of the concaved groove 18 of the main body portion 26 change, the slide-contact ring 19 also deforms in accordance with the groove bottom.

In this case, since processing of the groove bottom of the concaved groove 18 is easy, delicate adjustment of the shape of the outer circumferential surface of the slide-contact ring 19 is possible, rather than deforming the slide-contact ring 19, itself.

Figure 6:
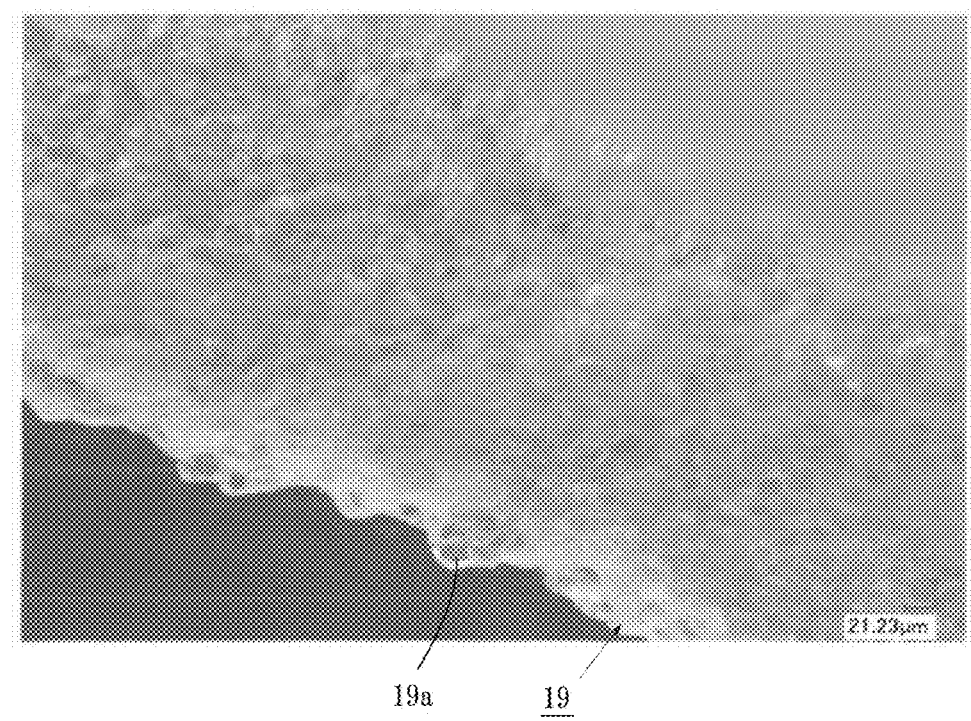
FIG. 6 is an enlarged substitutive picture of the silicone rubber of the present invention.

When the molded article (the slide-contact ring 19) obtained through molding using the metal mold was observed under a microscope (FIG. 6: enlarged picture), numerous particles of the ultrahigh molecular weight polyethylene fine particles 19a with various sizes were observed to being sticking to the surface of the molded article, and, to the gaps thereof, the thin film of the silicone rubber was observed to be sticking as if serving a role as an adhesive.

In addition, the silicone oil film 19b existed slightly on the surface of the ultrahigh molecular weight polyethylene fine particles 19a and the slide-contact ring 19 and displayed water repellency.

Furthermore, when one of the ultrahigh molecular weight polyethylene fine particles 19a in the molded article was poked with a needle-like object under the microscope, the ultrahigh molecular weight polyethylene fine particles 19a was observed to slightly move while sinking into the molded article.

As a result of this phenomenon, when the elastomer molded article was moved while having a slight pressure applied thereto, the elastomer molded article moved with an extremely small sliding resistance of 3 to 8 N (see entry regarding elastomer of the present invention at bottom of Table 1).

This is considered to be an expression of "slidability" that is unique to the present invention, as a result of a phenomenon regarding rolling of the ultrahigh molecular weight polyethylene fine particles 19a due to being easily rolled with assistance by the silicone oil and a continuous application lubrication phenomenon by the silicone oil.

Next, the slide-contact surface 11 of the main body portion 26 will be described.

As described above, for the main body portion 26, the drug solution-resistant rigid plastic is applied with respect to the drug solution 30 to be loaded in the syringe barrel 1. In the following, a case in which PTFE is used is described as an example.

For the method to obtain the above described shapes, although injection molding and cut-processing by using a lathe exist, only the cut-processing can be used for PTFE.

In the cut-processing, although any type of cutting tool may be used as long as the cutting tool can smoothly process the rigid plastic, a case will be described here as an example in which a monocrystal diamond is used and the cut-processing is performed with a generic small-size NC lathe.

PTFE (polytetrafluoroethylene) used as the processing material is cut-processed to obtain the gasket main body 26 shown in FIG. 1.

The width (defined as seal width S) of the slide-contact surface 11a of the liquid-contact side sliding part 16 of the gasket main body 26 having an important function regarding water tightness is cut out at 0.1 to 2.0 mm width (needless to say, the same shape can be manufactured through injection molding with a material other than PTFE).

Then, the slide-contact ring 19 described above is fitted in the concaved groove 18 of the gasket main body 26 to form the gasket 10.

The pre-filled syringe A as shown in FIG. 1 is formed by assembling the members described above, and loading the drug solution 30 in the space enclosed between the syringe barrel 1 and the gasket 10. For the loading of the drug solution, the vacuum loading method previously described is used in some cases, and a slidability (not larger than 8 N) that can support the method is demanded.

Similarly, the slidability (not larger than 8 N) is also demanded for manual injection as previously described.

On the other hand, with mechanical injection or loading of the drug solution with a plug assist method, a sufficient pressing force against the plunger rod 5 is not larger than 15 N.

In other words, the total sliding resistance of the pre-filled syringe A of the present invention is a sum of the sliding resistance of the slide-contact ring 19 and the sliding resistance of the gasket main body 26.

Since the sliding resistance of the slide-contact ring 19 is 4 to 8 N as described above, the above described force is calibrated to be not larger than 15 N or not larger than 8 N by adjusting the seal width S of the gasket main body 26 and the press-fit margin (half of the diameter difference) of the liquid-contact side sliding part 16 with respect to the syringe barrel 1.

When the pre-filled syringe A is used, usage preparation can be provided by simply taking off the top cap 8 and mounting a predetermined needle to the needle mount part 1b of the syringe barrel 1.

During usage, the motion of the plunger rod 5 is extremely smooth including the initial motion regardless of manual or mechanical usage.

Similarly, the gasket 10 including the slide-contact ring 19 maintains excellent slidability over an extended period of time not only at normal temperature because of the excellent water repellency and impermeability, but even after cold storage because of the noncreeping property of the slide-contact ring 19.

In addition, not only leakage of liquid but also penetration of vapor does not occur at the slide-contact surface 11a with respect to the inner circumferential surface 2 and the inside of the gasket 10.

It should be noted that the above described capabilities were satisfactory even after performing an accelerated test (6 month storage in environments at 5° C. and 40° C.) that takes into consideration of usage in various environments.

With this, it is possible to provide the pre-filled syringe A and the gasket 10 for syringe barrels without the need to apply a silicone oil on the syringe barrel inner circumference surface or use a medical-application plug covering film on the gasket, without being limited to size from small diameters to large diameters, at a low cost, and having sufficiently satisfactory high slidability, vapor impermeability, and water tightness such as leakage-less property when the pre-filled syringe A and the gasket 10 undergo storage not only at normal temperature but also at a low temperature (or usage at a high temperature).

The pre-filled syringe A described above but not being filled with the drug solution 30 is a disposable syringe. With the disposable syringe, the plunger rod 5 is drawn to suction the drug solution 30.

As a result, the gasket 10 mounted on the front end of the plunger rod 5 retreats from the front end side of the syringe barrel 1 to cause the drug solution 30 to be suctioned inside the space enclosed by the syringe barrel 1 and the gasket 10.

At this moment, the slide-contact ring 19 of the gasket 10 retreats while sliding on the inner surface of the syringe barrel 1.

Since there is an extremely thin layer of the silicone oil exuded on the surface of the slide-contact ring 19 loaded with the silicone oil, a transition layer of the silicone oil is thought to remain in a sliding mark on the inner surface of the syringe barrel 1.

However, when the syringe barrel 1 in which the gasket 10 was slidingly retreated was measured by using a chemical balance capable of detecting $\frac{1}{10,000}$ gram of the silicone oil, no residual silicone oil was detected.

From the fact described above, the gasket 10 according to the present invention was recognized as to be applicable not only to the pre-filled syringe A but also to a disposable syringe. EXAMPLES (1) Manufacturing Slide-Contact Ring and Slidable Silicone Rubber of Present Invention A slidable silicone rubber of the present invention was formed by using "a liquid or greasy, or clayish organopolysiloxane having a small molecular weight" as a silicone rubber material, adding 25% silica fine powder to obtain a silicone rubber base material (plasticity number: 180 (measured with Williams plastometer)), adding thereto the ultrahigh molecular weight polyethylene fine powder (additionally, the silicone oil), and kneading the mixture with a kneader. The blend ratio of each component is as shown in Table 2.

The curing catalyst is any one of platinum or rhodium, or an organic compound of tin in the case with the addition reaction-type slidable silicone rubber, and is a peroxide in the case with the peroxide cross-linking type slidable silicone rubber.

The slide-contact ring was molded with a method of loading the slidable silicone rubber in a cavity capable of molding a slide-contact ring having the above described shape, and heating and pressurizing the compression metal mold at, for example, 140° C. to 150° C. for a curing time of 5 minutes. With this, the target slide-contact ring was obtained. Heating (annealing) was additionally performed thereon at 130° C. for 8 hours.

(2) Slidability Test of Slidable Silicone Rubber of Present Invention (Table 2)

Figure 7:
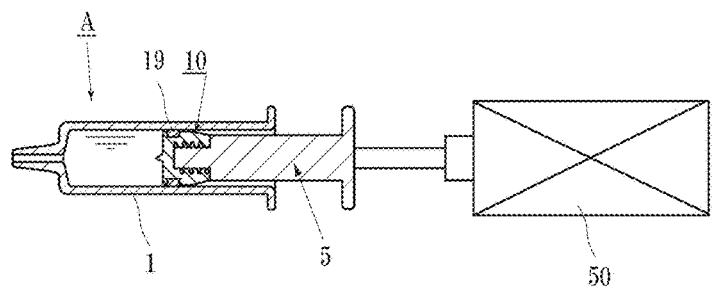
FIG. 7 is a schematic diagram showing how measurement of the sliding resistance of a gasket of the present invention is performed.

In the present test, the slide-contact ring 19 had an outer diameter of 6.4 mm, an internal diameter of 4.5 mm, and a length of 2.5 mm. The slide-contact ring formed in such manner was mounted on a gasket main body (diameter× length of concaved groove=4.5 (in diameter)×2.7 mm), and the "sliding resistance" thereof was measured by using a sliding resistance measuring device shown in FIG. 7.

In this case, for the purpose of measuring the sliding resistance of the slide-contact ring alone, a dimension in which the gasket main body does not contact the syringe barrel inner circumference surface was used.

Figure 8:
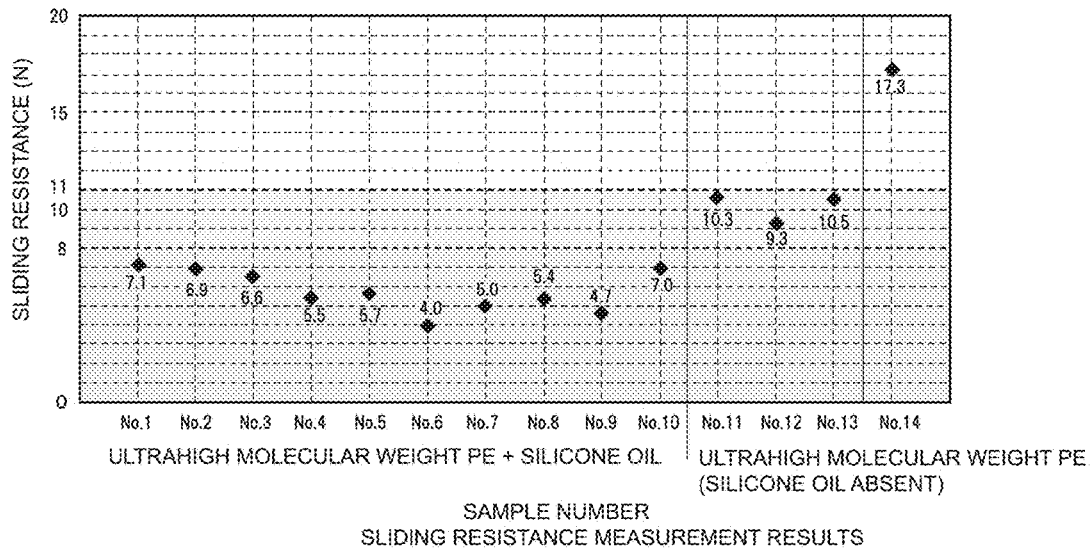
FIG. 8 is a graph showing the change in sliding resistance of the gasket (composition change) of the present invention.

The measurement results are as shown in Table 2 and FIG. 8.

Although the sliding resistance varies depending on the formulation, the sliding resistance was 9 to 11 N with the "ultrahigh molecular weight polyethylene fine powder" alone.

When "a silicone grease added to the rubber" was used in combination, the sliding resistance was 4 to 8 N.

(3) Slidability Test of Gasket Main Body Itself

Syringe barrel made from COP: Internal diameter=6.20 mm (10 barrels)

PTFE gasket main body (no slide-contact ring)
Seal width: 3 types of 0.1, 0.6, 2 mm
Diameter difference S: 4 types of 300, 150, 100, and 10 µm for 0.1 mm;
3 types of 200, 150, and 100 µm for 0.6 mm; and
4 types of 150, 60, 40, and 20 µm for 2 mm.

Figure 9:
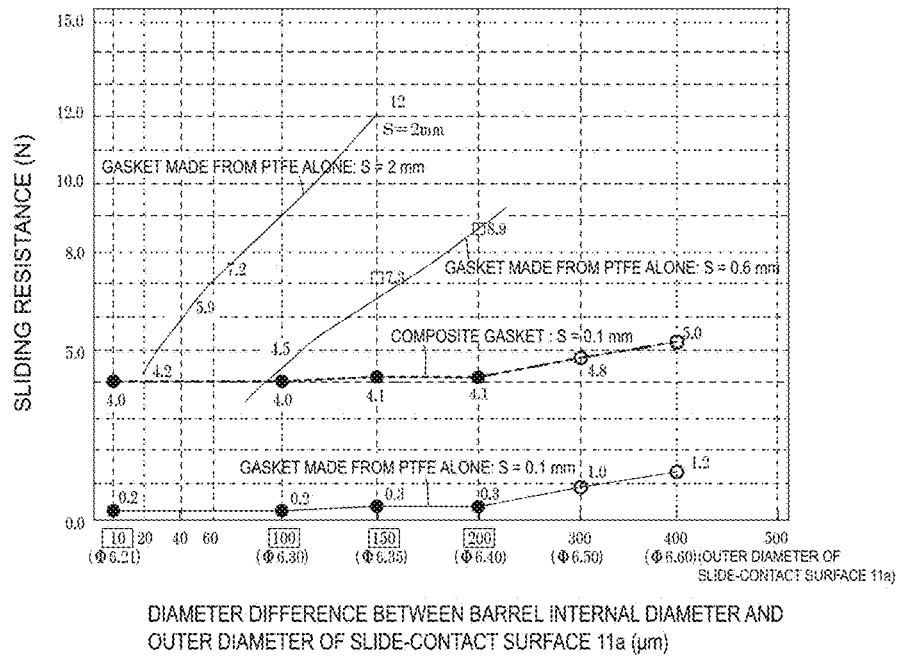
FIG. 9 is a graph showing the change in sliding resistance related to the seal width of a PTFE gasket.

The sliding resistance is as shown in FIG. 9. For comparison, a composite gasket (seal width=0.1 mm) in FIG. 10 was also described therein.

(4) Composite Gasket (Gasket Main Body Having Slide-Contact Ring Mounted Thereon: Sliding Resistance of Composite Gasket=Sliding Resistance of Gasket Main Body+ Sliding Resistance of Slide-Contact Ring) (FIGS. 9 to 11)

Figure 10:
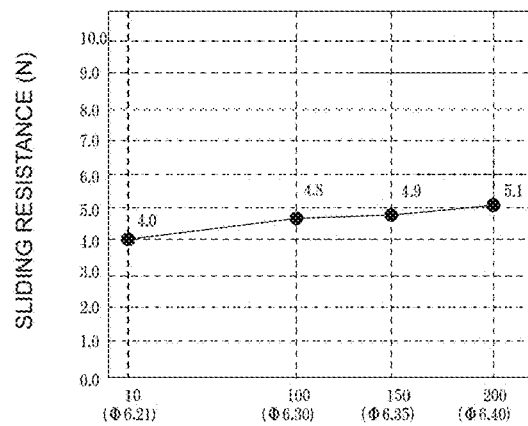
FIG. 10 is a graph showing the change in sliding resistance related to a seal width (0.1 mm) of a composite gasket.

The composite gasket (seal width S=0.1 mm) in FIG. 10 had a sliding resistance of 5.1 N when the diameter difference between the internal diameter of the syringe barrel and the outer diameter of the seal portion was 200 µm, and can be applied for manual injection.

Figure 11:
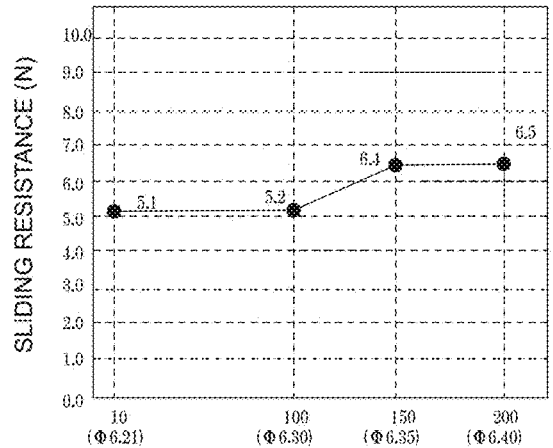
FIG. 11 is a graph showing the change in sliding resistance related to a seal width (0.2 mm) of the composite gasket.
Figure 12:
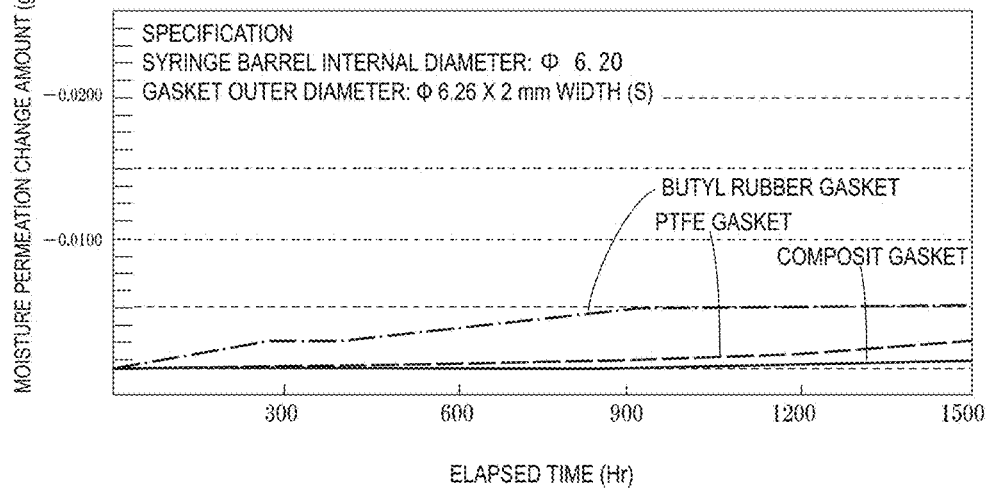
FIG. 12 is a graph (seal width: 0.2 mm) showing the results of water vapor permeability evaluation of the present invention (composite gasket) and conventional gaskets (PTFE, butyl rubber).

A composite gasket (seal width S=0.2 mm) in FIG. 11 had a sliding resistance of 6.5 N when the diameter difference was 200 µm, and can also be applied for manual injection.

Based on the test results, in a case where the sliding resistance of the syringe barrel using the composite gasket is 8 N, a seal width S up to 0.3 mm is considered applicable when the diameter difference is 200 µm. When the seal width S is 0.3 mm or larger, the diameter difference is gradually reduced from 200 µm.

On the other hand, in a case where the sliding resistance of the composite gasket is set to 15 N, since the sliding resistance of the slide-contact ring is 9 to 13 N with "the ultrahigh molecular weight polyethylene fine powder" alone and 4 to 8 N when "the ultrahigh molecular weight polyethylene fine powder and the silicone grease" are used in combination as described above; the value obtained by subtracting the sliding resistance of the slide-contact ring from the maximum pressing force with respect to the plunger rod of 15 N becomes the sliding resistance allowed on the gasket side, and a gasket main body displaying a value within this range is to be selected.

Figure 4A:
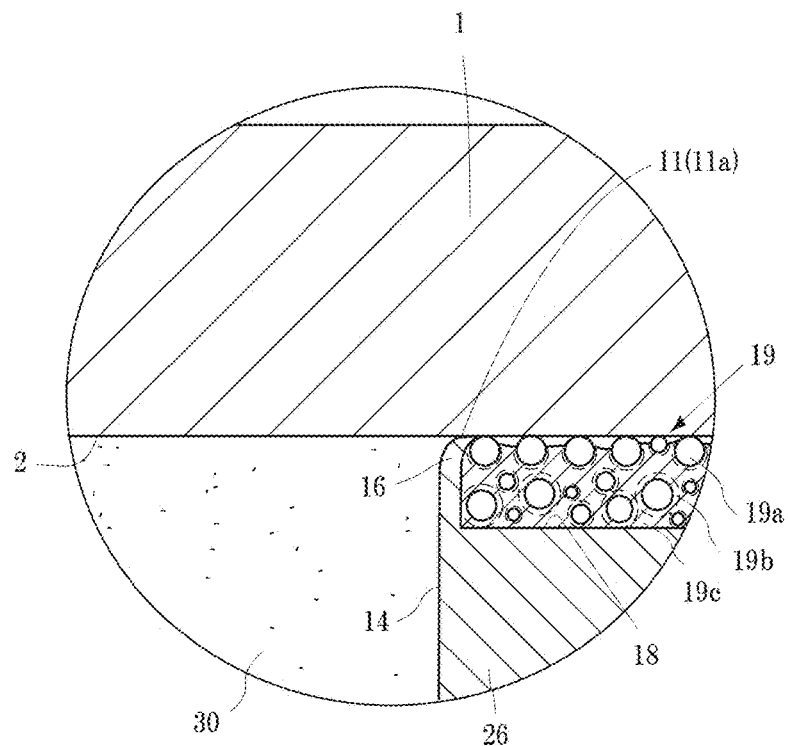
In FIG. 4, (A) and (B) are each an enlarged front view showing a portion shown with an ellipse drawn by a broken line in FIG. 2.
Figure 4B:
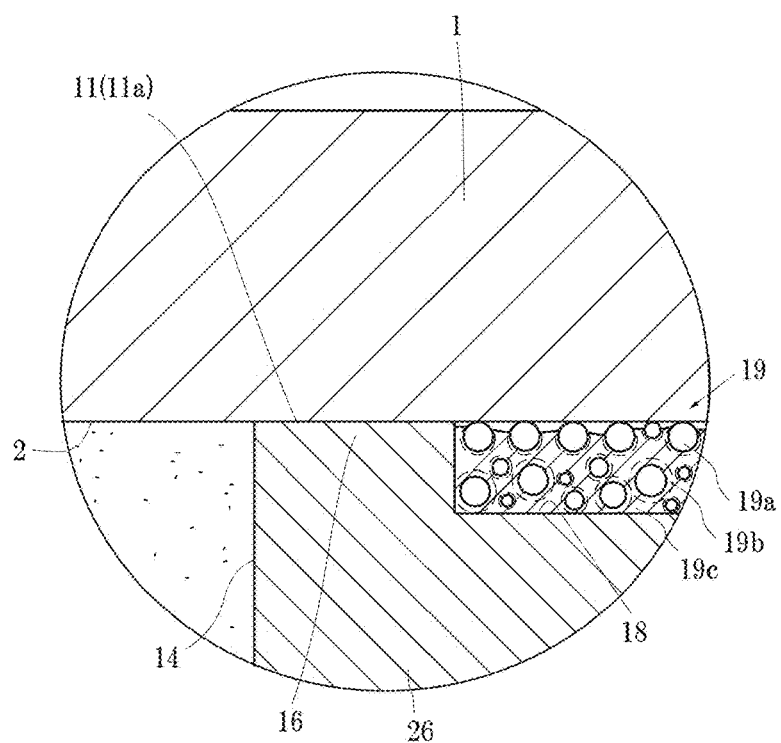
Figure 5:
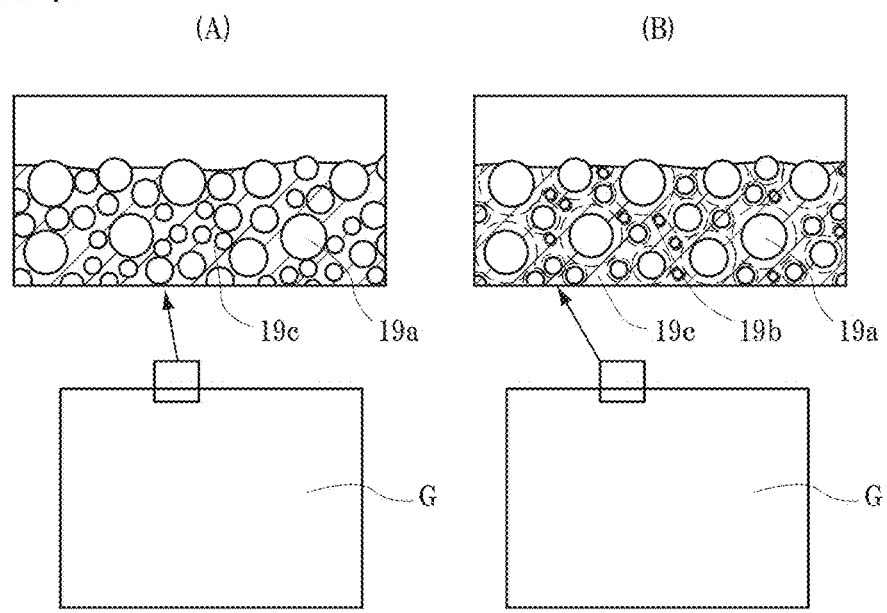
In FIG. 5, (A) and (B) are respectively a front view of a silicone rubber of the present invention and an enlarged cross sectional view of one portion thereof.

In FIG. 9, if the seal width S is small, a fine slidability is observed even when the press-fit margin (half of the diameter difference) is quite large as 200 µm. It should be noted that, also if the seal width S is small with a rigid plastic other than PTFE, a fine slidability is observed even when the press-fit margin (half of the diameter difference) is quite large. This is because, since the liquid-contact side sliding part which is the seal portion is in a film form, the front end edge of the liquid-contact side sliding part, while being backed up by elasticity of the slide-contact ring on the back surface, is pressed against the syringe barrel inner circumference surface, deforms, and adheres closely to the inner circumferential surface of the syringe barrel ((A) of FIG. 4). Although the shape can be considered to have some shortcomings in terms of sliding stability because the seal width S is extremely small, the sliding stability can be improved by creatively setting the length and shape of the sliding ring and the level of slide-contact of the sliding surface on the plunger rod 5 side of the gasket main body with respect to the syringe barrel inner circumference surface. When a contact is made through an edge, the thin liquid-contact side sliding part is bent and the edge portion on the liquid contact side of the liquid-contact side sliding part makes contact to show a good water-stopping ability.

It should be noted that the seal width S can be increased up to 2 mm as described above. When the seal width S is increased from 0.1 mm to 2 mm, the strength of the liquid contact surface side sliding part gradually increases and the contact through the edge as described above is obtained up to a width of about 0.6 mm. When the width exceeds that, the strength gradually increases to cause the liquid contact side slide-contact surface of the liquid-contact side sliding part to strongly contact the syringe barrel inner circumference surface. Thus, in order to limit the sliding resistance to be not larger than 15 N (not larger than 8 N for manual operation), the press-fit margin with respect to the syringe barrel inner circumference surface has to be gradually decreased.

In this case, when the gasket main body is formed through cutting, fine and shallow linearly cut grooves are generated on the liquid contact surface side slide-contact surface which is most important. However, as long as the cutting pitch and the depth of the grooves are sufficiently small (e.g., cutting pitch being not larger than 40 μm and the groove depth being not larger than 6 μm), a cold flow is generated in the slide-contact surface by the pressure against the syringe barrel inner circumference surface to eliminate the linearly cut grooves and achieve a good water cutoff. Such a slide-contact surface is not generated when injection molding is used.

Water-Vapor Permeation Test

Measurement results: The composite gasket showed excellent impermeability when compared to, not only a conventionally used butyl rubber gasket, but also a PTFE gasket entirely created from PTFE having excellent impermeability. With the PTFE gasket, the main reason of leakage of vapor is thought to be from the syringe barrel inner circumference surface and the sealing surface of the PTFE gasket. With the composite gasket of the present invention, leakage of vapor from the syringe barrel inner circumference surface and the sealing surface of the PTFE gasket is thought to be further limited as a result of having high rubber elasticity and excellent impermeability and using the ultrahigh molecular weight PE fine particles having a large particle size distribution in a closely packed state.

DESCRIPTION OF THE REFERENCE CHARACTERS

A pre-filled syringe
S seal width
φ internal diameter of syringe barrel
1 syringe barrel
1a barrel main body
1b needle mount part
1c flange
2 inner circumferential surface
5 plunger rod
5a male-screw part
5b finger rest part
8 top cap
8a cap main body
8b concaved portion
8c engagement protrusion
10 gasket
11 slide-contact surface
11a slide-contact surface on liquid contact surface side
11b sliding surface on plunger rod side
14 liquid contact surface
15 female-screw hole
16 liquid-contact side sliding part
17 tapered portion
17a mount surface of plunger rod
18 concaved groove
19 slide-contact ring
19a fine particle
19b silicone oil film
19c silicone rubber base material
26 main body portion (gasket main body)
30 drug solution
31 drug

The invention claimed is:

1. A gasket, for syringes, to be press-fitted in a syringe barrel and used in a slidable manner, the gasket comprising:
a main body portion that is formed of a rigid plastic having a drug solution-resistant property against a drug solution to be loaded in the syringe barrel, and that has a slide-contact surface that slidingly contacts an inner circumferential surface of the syringe barrel; and
a slide-contact ring that is fitted in a concaved groove formed over a whole circumference of the slide-contact surface, and is configured to slidingly contact the inner circumferential surface of the syringe barrel, wherein
within the slide-contact surface, at least a slide-contact surface adjacent to a liquid contact surface with respect to the drug solution is formed to be in contact with the inner circumferential surface and liquid-tight with respect to the inner circumferential surface,
the main body has a liquid-contact side sliding part having the liquid contact surface, the slide-contact surface adjacent to the liquid contact surface, and a back surface contacting the slide-contact ring,
the slide-contact ring is disposed in contact with the back surface of the liquid-contact side sliding part so as to back up the liquid-contact side sliding part,
the slide-contact ring is formed of a slidable silicone rubber obtained by adding a spherical ultrahigh molecular weight polyethylene fine powder to a silicone rubber base material, a filler being added to the silicone rubber base material, wherein a silicone oil is optionally added to the slidable silicone rubber of the slide-contact ring,
when the silicone oil is not added, the slidable silicone rubber contains, in volume ratio, the ultrahigh molecular weight polyethylene fine powder by 44.5 to 60% and the silicone rubber base material containing the filler for a remaining portion, and
when the silicone oil is added, the slidable silicone rubber contains, in volume ratio, the ultrahigh molecular weight polyethylene fine powder by 30 to 65%, the silicone oil by 7 to 40%, a total of the ultrahigh molecular weight polyethylene fine powder and the silicone oil being 37 to 72%, and the silicone rubber base material containing the filler for a remaining portion.

2. The gasket for syringes according to claim 1, wherein the silicone oil is added to the slidable silicone rubber of the slide-contact ring.

3. The gasket for syringes according to claim 1, wherein a range of particle sizes of the ultrahigh molecular weight polyethylene fine particles is from 10 to 300 μm.

4. The gasket for syringes according to claim 1, wherein a material of the silicone rubber base material is obtained by thermally curing an amorphous polysiloxane having a vinyl group incorporated in a molecule thereof and an amorphous polysiloxane having a reactive hydrogen incorporated at a molecule terminal thereof, through a reaction using, as a catalyst, any one of platinum, rhodium, or an organic compound of tin.

5. The gasket for syringes according to claim 1, wherein a material of the silicone rubber base material is obtained through a curing reaction of a polysiloxane having a vinyl group incorporated therein by using a peroxide as a curing catalyst.

6. The gasket for syringes according to claim 1, wherein, the filler including a fine-particle silica as a main component and at least one of a PTFE fine powder, glass beads, talc, a titanium powder, or carbon, is added to the silicone rubber base material.

7. The gasket for syringes according to claim 1, wherein the slide-contact ring is obtained by heating at a temperature not higher than 130° C. for 4 to 24 hours.

8. The gasket for syringes according to claim 1, wherein a width of the slide-contact surface of the liquid-contact side sliding part is 0.1 to 2 mm.

9. The gasket for syringes according to claim 1, wherein the main body portion of the gasket is a closed-cell PTFE.

10. A syringe comprising a syringe barrel to be filled with a drug solution, the gasket, according to claim 1, press-fitted inside the syringe barrel, and a plunger rod mounted in the gasket.

* * * * *